United States Patent [19]

Becker et al.

[11] Patent Number: 5,264,634

[45] Date of Patent: Nov. 23, 1993

[54] VOLATILE ALKALINE EARTH METAL COMPLEX AND ITS USE

[75] Inventors: Winfried Becker, Kelkheim; Stephan Weidlich, Frankfurt am Main, both of Fed. Rep. of Germany

[73] Assignee: Hoechst Aktiengesellschaft, Frankfurt am Main, Fed. Rep. of Germany

[21] Appl. No.: 864,513

[22] Filed: Apr. 7, 1992

[30] Foreign Application Priority Data

Apr. 9, 1991 [DE] Fed. Rep. of Germany ....... 4111460

[51] Int. Cl.$^5$ .............................................. C07C 49/12
[52] U.S. Cl. .................... 568/413; 568/412; 568/410
[58] Field of Search ............. 568/412, 413, 410

[56] References Cited

U.S. PATENT DOCUMENTS 4,558,144 12/1985 Fay et al. ............................ 568/412

OTHER PUBLICATIONS

Eisentraut et al, J.A.C.S., vol. 87, pp. 5254–5256 (1965).
Timmer et al, Chem. Abst., vol. 116, #33263e (1992).
Rassetto et al, Polyhedron, vol. 11, pp. 979–985 (1992).
Hammond et al, Inorg. Chem., vol. 2, p. 73 (1963).
Norman et al., *J. Chem. Soc. Chem. Commun.*, pp. 971–972, (1991).
Greenwood et al., *Chemie der Elemente*, VCH Verlagsgesellschaft, Weinheim (1990) p. 137.

*Primary Examiner*—James H. Reamer
*Attorney, Agent, or Firm*—Curtis, Morris & Safford

[57] ABSTRACT

An alkaline earth metal chelate complex of 2,2,6,6-tetramethylheptanedione of the formula (I)

$$M^{2+}(C_{11}H_{19}O_2)^{-}_2 \cdot L_k \qquad (I)$$

is described, in which M is calcium, strontium or barium, L is a ligand and k is a number from 1 to 3, the complex being free of water of hydration and the ligand L being an aliphatic ether having at least two oxygen atoms in the molecule. A process for the preparation of the chelate complex and its use for the production of coated substrates are also described.

4 Claims, 2 Drawing Sheets

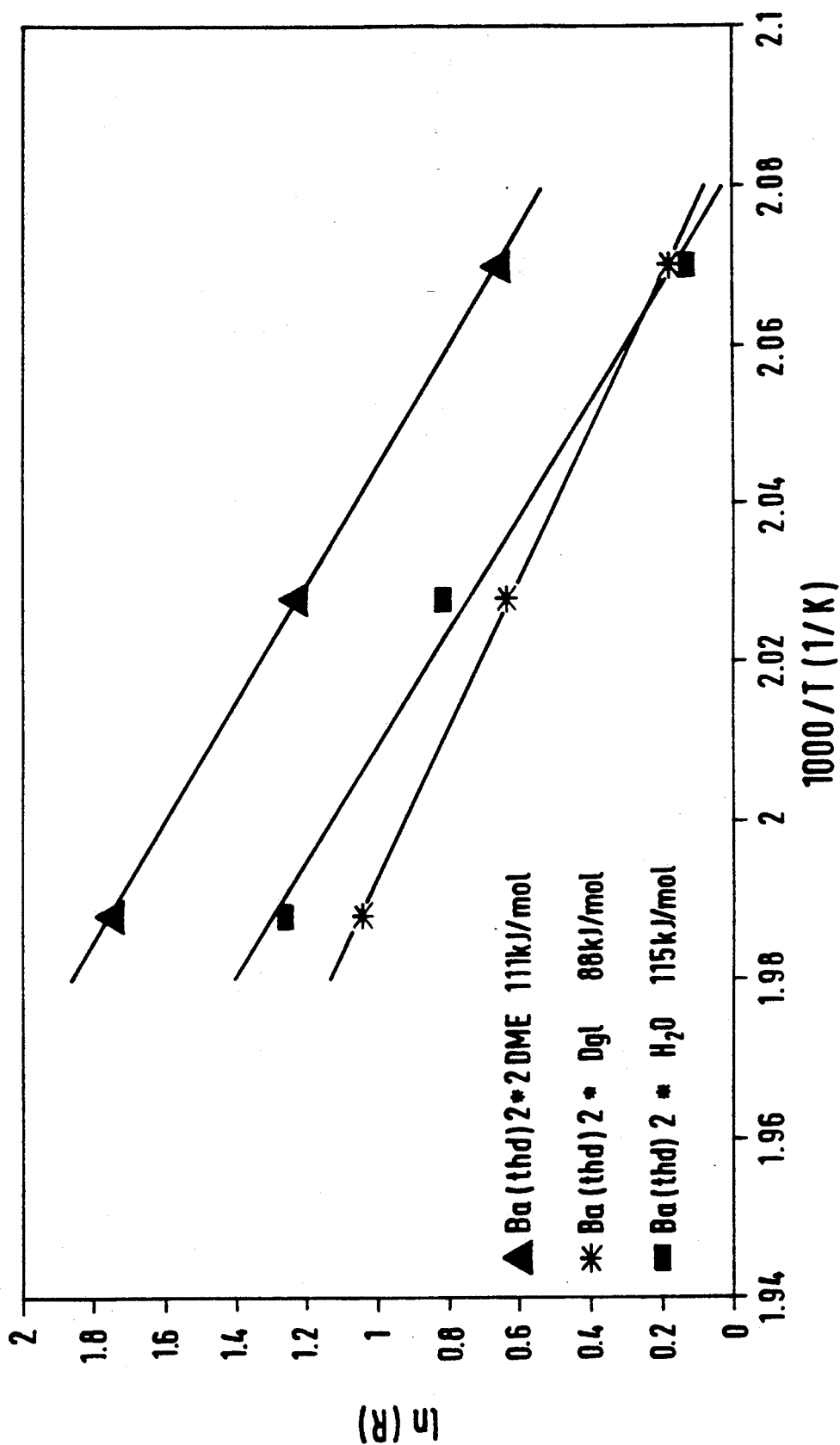
Fig. 1 ARRHENIUS-PLOT OF EVAPORATION RATES OF DISSOLVED Ba(thd)

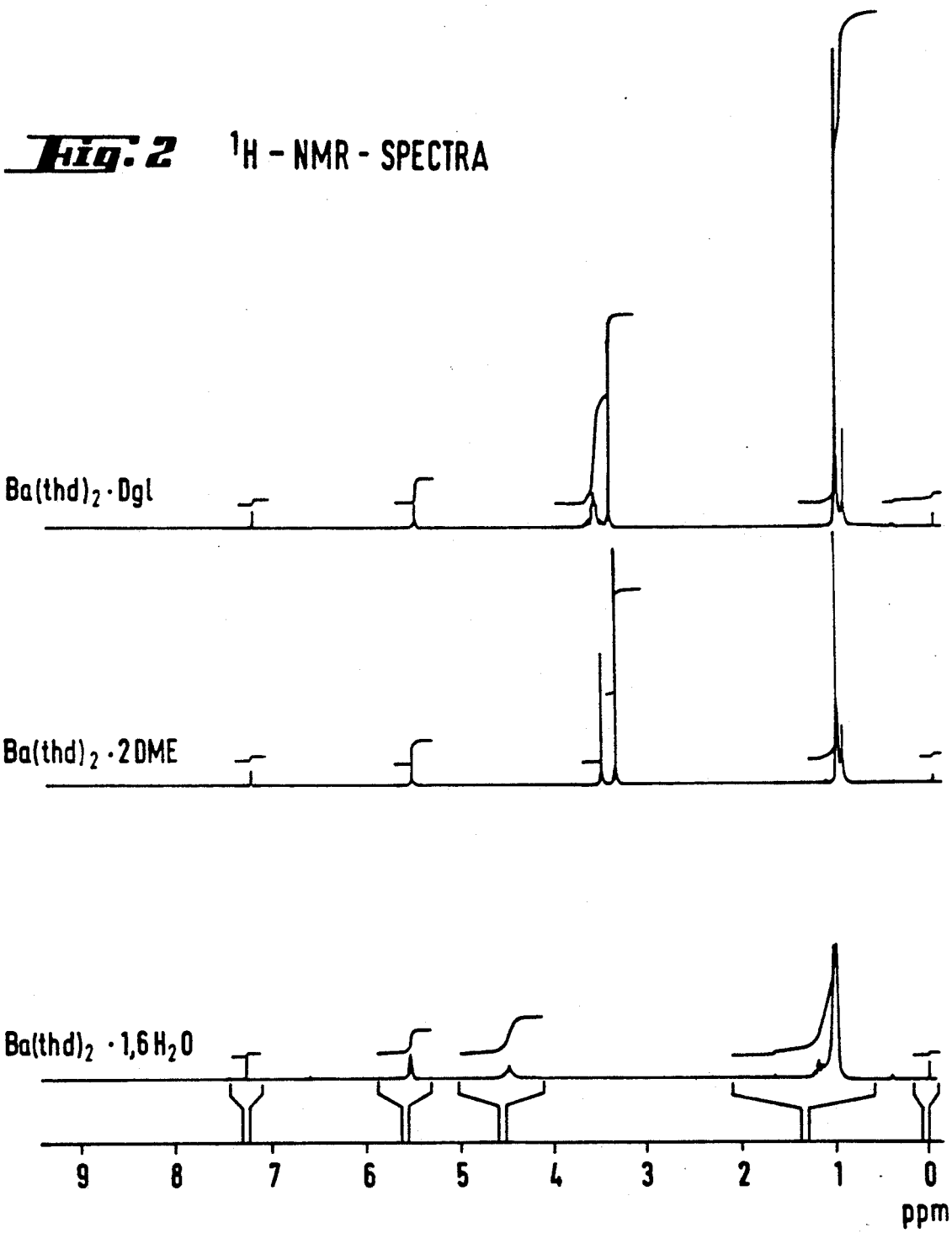

VOLATILE ALKALINE EARTH METAL COMPLEX AND ITS USE

DESCRIPTION

The invention relates to an alkaline earth metal chelate complex of 2,2,6,6-tetramethylheptanedione containing aliphatic ethers as complexing ligands and thus having particularly high volatility. Furthermore, the invention relates to the use of this chelate complex for the coating of substrates with a high-temperature superconductor material containing alkaline earth metals.

Since the discovery of the superconducting properties of lanthanum barium cuprate by Bednorz and Müller further superconducting oxide ceramics have been discovered in large numbers, in some cases with temperatures above the boiling temperature of nitrogen. They are therefore of great technical interest.

The new superconductors made of oxide ceramic have a granular structure. The grain boundaries are so-called weak links for the superconducting current, which limit the critical current densities in polycrystalline ceramics to about 1000 A/cm$^2$ in a zero-voltage field and lead to a high dependence of the critical current densities on the magnetic field. These disadvantages of granular structure are not observed in epitaxial layers, due to the absence of grain boundaries. Accordingly, the attempt has been made to produce thin monocrystalline layers by physical processes, for example by sputtering or laser ablation. Compared with these processes, the process of metal organic chemical vapor deposition (MOCVD) has a number of advantages: deposition takes place at a reduced pressure of about 10 mbar and accordingly does not require an expensive high-vacuum plant. Moreover, coating involves extensive scattering, as a result of which it is possible to coat not only substrates of complicated geometrical structure on their entire surface but also large areas uniformly.

The disadvantage of this method is the heat sensitivity of the starting compounds used, in particular of those containing the alkaline earth metals Ca, Sr and Ba. These compounds have to be volatile at 10 mbar at temperatures of up to 250° C. For example, German Offenlegungsschrift 3,827,069 discloses that the compounds used for preparing YBa$_2$Cu$_3$O$_x$ include the barium chelate complex of 2,2,6,6-tetramethylheptanedione.

However, it has been found that the known alkaline earth metal chelate complexes of 2,2,6,6-tetramethylheptanedione decompose noticeably even during evaporation and their evaporation temperature varies from charge to charge in a non-reproducible manner. This makes precise process control difficult in practice and increases the waste. These difficulties are pointed out, for example, in Superconductor Week, Sep. 10, 1990, p. 2-3.

The synthesis of chelate compounds of rare earths derived from 2,2,6,6-tetramethylheptanedione is known per se and is described by K. J. Eisentraut et al., J. Am. Chem. Soc. 87 (1965) 5254. This synthesis is carried out by dissolving a rare earth salt, the heptanedione mentioned and a base in ethanol/water, combining the solutions and precipitating the chelate compound by addition of water. The rare earth chelates crystallize free of water of hydration. The process can also be applied to the preparation of analogous chelate compounds of alkaline earth metals.

G. S. Hammond et al., Inorg. Chem. 2 (1963) 73 describe a method for the preparation of barium chelates of 2,2,6,6-tetramethylheptanedione, in which the latter is shaken with an aqueous solution of Ba(OH)$_2$ until the diketone phase has disappeared and the barium chelate has precipitated.

More detailed studies have shown that the reaction products in these processes still contain water of hydration, adhering water (moisture), unconverted free diketone ligands and starting salts, for example barium hydroxide and/or barium nitrate, as impurities. Recrystallisation removes the free ligand and adhering salts; the moisture, but not the water of hydration present, can be removed by drying in vacuo. Upon evaporation in the CVD process, the substances melt in their own water of hydration, which also leads to hydrolysis. This is why evaporation residues of 20 to 30% of the amount originally weighed and substantially comprising barium oxide or barium hydroxide are quite frequent.

Accordingly, the object of the invention was to find new alkaline earth metal compounds showing constant rates of evaporation and being in particular more volatile, so that they can be deposited in a more controllable fashion.

This object is achieved by means of alkaline earth metal salts of 2,2,6,6-heptamethylheptanedione of the formula I

$$M^{2+}(C_{11}H_{19}O_2)^{-}{}_2 \cdot L_k \qquad (I)$$

in which M is calcium, strontium and in particular barium, L is a ligand and k is a number from 1 to 3, the salts being free of water of hydration and containing an aliphatic ether having at least two oxygen atoms in the molecule as ligand L. Preferably, the aliphatic ether is a bis(methyl) ether or bis(ethyl) ether, in particular of ethylene glycol or diethylene glycol. Ethers of tri- and tetraethylene glycol are also suitable.

The alkaline earth metal chelate complexes according to the invention can be prepared by recrystallizing an alkaline earth metal chelate complex of 2,2,6,6-tetramethylheptanedione containing water of hydration from an aliphatic ether having at least two oxygen atoms in the molecule. Recrystallization completely displaces the previous water of hydration from the coordination sphere and replaces it by the ether ligand. In most cases, the ether content varies between 1.5 and 2.3 molecules per formula unit and depends substantially on the concentration during recrystallization. The more concentrated the solution, the less ether there is in the compound.

Since the new compounds do not contain water, no hydrolysis can take place during evaporation. Evaporation in the MOCVD process therefore proceeds in a stable manner over a period of several hours. Under dry conditions, the new compounds have an unlimited shelf life. Unlike water, the ethers used according to the invention are polydentate ligands. This leads to easier saturation of the coordination sphere of the alkaline earth metal, resulting in lower evaporation temperatures, good yields and good reproducibility in the CVD process.

FIG. 1 shows the Arrhenius plots of Ba(thd)$_2$ solvates in water, 1,2-dimethoxyethane (DME) and diethylene glycol dimethyl ether (Dgl) and the energies of activation for the evaporation calculated from the straight line slopes. They show that although the hydrate and the DME etherate have approximately the same energies of activation, the etherate nevertheless shows rates of evaporation of about 50% higher.

Although the Dgl etherate shows the same rates of evaporation as the hydrate, it nevertheless has a lower energy of activation. This leads to better reproducibility of the coating results, since variations in the evaporation temperature affect the variations in the rates to a lesser extent.

Accordingly, the alkaline earth metal chelate complexes according to the invention are highly suitable for the MOCVD process. They are very particularly suitable for a process for the coating of an inert substrate with a high-temperature superconductor containing barium, calcium or strontium. In this process, volatile compounds of the individual metals which make up the high-temperature superconductor are heated to different temperatures in separate evaporators, the vapor formed together with an inert carrier gas is combined with an oxygen stream, and the gas mixture is subjected to pyrolysis on a hot substrate surface of about 850° C., resulting in deposition of the metal oxides on the substrate. The coated substrate is then cooled slowly, preferably over a period of one hour, to room temperature in an oxygen-containing atmosphere. In another embodiment of the invention, the gas mixture is subjected to pyrolysis at about 850° C., and the hot pyrolysis gases are deposited on a cooled substrate. The coated substrate is then heated in an oxygen-containing atmosphere over a period of at least one hour. The purpose of this treatment is to increase the oxygen content of the coating to such an extent that a superconductor is present. The volatile alkaline earth metal compound used in this process is an alkaline earth metal chelate complex according to the invention. A preferred device for the production of thin metal mixed oxide films comprising organic metal compounds on a substrate by the CVD process is disclosed in German Patent Application, laid open for public inspection.

The superconductors deposited according to the invention and containing alkaline earth metals, for example $Bi_2Sr_2CaCu_2O_8$ or $Bi_2Sr_2Ca_2Cu_3O_{20}$ are cooled in an $O_2$-containing atmosphere. In the case of compounds of the $YBa_2Cu_3O_7$ type, heating in an oxygen-containing atmosphere must take place over an extended period of time, in order to complete conversion into the orthorhombic phase. A suitable procedure for achieving this is, for example, a holding step of 10 to 30 minutes at 400°–500° C.

The invention is illustrated in more detail by the examples, in which "thd" is the 2,2,6,6-tetramethylheptanedione anion and "DME" is 1,2-dimethoxyethane.

EXAMPLE 1

25.55 g of $Ba(thd)_2 \times 0.8$ $H_2O$ are dissolved at room temperature in 175 ml of 1,2-dimethoxyethane (=146 g/l). In a refrigerator at 8° C., colorless cuboid crystals precipitate. The supernatant solution is removed in the cold (for example by means of a pipette), and any adhering liquid is removed from the crystals in vacuo. Yield: 18.3 g of $Ba(thd)_2 \times 1.60$ DME.

EXAMPLE 2

Procedure as in Example 1. 20 g of $Ba(thd)_20.75$ $H_2O$, 300 ml of 1,2-dimethoxyethane (=67 g/l), precipitation in the freezer compartment at −18° C.

Yield: 14.8 g of $Ba(thd)_2 \times 2.27$ DME.

EXAMPLE 3

10 g of $Ba(thd)_2 \times 0.3$ $H_2O$ are dissolved at 60° C. in 20 ml of diethylene glycol dimethyl ether (=500 g/l). In a refrigerator at 8° C., colorless cuboid crystals precipitate. The supernatant solution is removed in the cold (for example by means of a pipette), and any adhering liquid is removed from the crystals in vacuo.

Yield: 10.2 g of $Ba(thd)_2 \times 1.52$ Dgl (Dgl=diethylene glycol dimethyl ether).

The nuclear magnetic resonance spectra ($^1$H NMR spectra at 100 MHz, solvent $CDCl_3$/TMS) of the compounds can be seen from FIG. 2, and their evaporation properties from FIG. 1. In these figures, R is the rate of evaporation of various barium chelates [mg/min] measured via the weight loss. FIG. 1 also shows the energy of activation for evaporation of the compounds determined from the straight lines and calculated from the Arrhenius equation.

We claim:

1. An alkaline earth metal chelate complex of 2,2,6,6-tetramethylheptanedione of the formula (I)

$$M^{2+}(C_{11}H_{19}O_2)^-{}_2 \cdot L_k \qquad (I)$$

in which M is calcium, strontium or barium, L is a ligand and k is a number from 1 to 3, the complex being free of water of hydration and the ligand L being an aliphatic ether having at least two oxygen atoms in the molecule.

2. A chelate complex as claimed in claim 1, wherein the aliphatic ether is a bis(methyl) ether or a bis(ethyl) ether.

3. A chelate complex as claimed in claim 2, wherein the aliphatic ether is a bis ether or ethylene glycol or diethylene glycol.

4. A process for the preparation of an alkaline earth metal chelate complex as claimed in claim 1, which comprises recrystallizing an alkaline earth metal chelate complex of 2,2,6,6-tetramethylheptanedione containing water of hydration from an aliphatic ether having at least two oxygen atoms in the molecule.

* * * * *